(12) United States Patent
Yoshida et al.

(10) Patent No.: US 8,038,861 B2
(45) Date of Patent: Oct. 18, 2011

(54) LAMINATED GAS SENSOR ELEMENT AND GAS SENSOR

(75) Inventors: Shin Yoshida, Aichi (JP); Nobuo Furuta, Kasugai (JP); Yuya Nakayama, Kasugai (JP)

(73) Assignee: NGK Spark Plug Co., Ltd., Aichi (JP)

( * ) Notice: Subject to any disclaimer, the term of this patent is extended or adjusted under 35 U.S.C. 154(b) by 393 days.

(21) Appl. No.: 12/423,039

(22) Filed: Apr. 14, 2009

(65) Prior Publication Data

US 2009/0255812 A1    Oct. 15, 2009

(30) Foreign Application Priority Data

Apr. 14, 2008   (JP) .................................. 2008-104394

(51) Int. Cl.
*G01N 27/417*   (2006.01)
*G01N 27/419*   (2006.01)

(52) U.S. Cl. .................. 204/429; 204/426; 204/428
(58) Field of Classification Search .................. 204/424, 204/426, 427, 429, 428
See application file for complete search history.

(56) References Cited

U.S. PATENT DOCUMENTS

| 5,144,249 | A | * | 9/1992 | Kurishita et al. | 324/439 |
| 5,630,920 | A | * | 5/1997 | Friese et al. | 204/424 |
| 5,676,811 | A | * | 10/1997 | Makino et al. | 204/425 |
| 6,022,464 | A | * | 2/2000 | Schumann | 204/424 |
| 7,867,370 | B2 | * | 1/2011 | Tsuji et al. | 204/429 |
| 7,887,684 | B2 | * | 2/2011 | Awano et al. | 204/426 |
| 2011/0056832 | A1 | * | 3/2011 | Muraoka et al. | 204/424 |

FOREIGN PATENT DOCUMENTS

| JP | 2003-322632 A | 11/2003 |
| JP | 2006-343297 A | 12/2006 |

* cited by examiner

*Primary Examiner* — Bruce Bell
(74) *Attorney, Agent, or Firm* — Sughrue Mion, PLLC

(57) ABSTRACT

A laminated gas sensor element extending in a longitudinal direction and having a detection part including a plate-shaped element body which has a heater layer having an embedded resistance heating body and a detection layer laminated to the heater layer and having a vertical surface along a lamination direction and a horizontal surface perpendicular to the lamination direction; and a porous protective layer coating the vertical surface and the horizontal surface of the element body constituting the detection part, wherein a thickness of the protective layer formed on the vertical surface is thicker than a thickness of the protective layer formed on the horizontal surface.

13 Claims, 5 Drawing Sheets

LAMINATED GAS SENSOR ELEMENT AND GAS SENSOR

BACKGROUND OF THE INVENTION

1. Field of the Invention

The present invention relates to a laminated gas sensor element and a gas sensor incorporating the laminated gas sensor element.

2. Description of the Related Art

A laminated gas sensor element is known as an element of a gas sensor for measuring a concentration or detecting a specific gas component contained in the exhaust gas of an internal combustion engine, etc. Since a solid electrolyte such as zirconia used in this laminated gas sensor element becomes active at a high temperature of 300° C. or more, the solid electrolyte is normally used in a state in which it is heated by a heater laminated to the solid electrolyte. As a result, when oil drops or water drops in a measuring object gas adhere to the gas sensor element, cracking sometimes occurs due to thermal shock. A technique for protecting a detection part of the gas sensor element exposed to the measuring object gas by means of a porous protective layer is known in order to solve this problem. For example, a technique for preventing the occurrence of cracking by thickening a protective layer in the corner of a gas sensor element is known (Patent Reference 1). Also, a technique for suppressing an increase in volume and suppressing thermal shock by making a horizontal width dimension of the top of a gas sensor element having a detection part smaller than that of the other portion and coating a surface along a lamination direction with a protective layer is known (Patent Reference 2).

[Patent Reference 1] JP-A-2003-322632
[Patent Reference 2] JP-A-2006-343297

3. Problems Solved by the Invention

However, the above described techniques have a few disadvantages. That is, the inventor of the present application found that cracking tends to occur at a boundary part between layers constituting a gas sensor element. Concretely, when a protective layer is not formed at the boundary part and the boundary part is exposed or a protective layer with a sufficient thickness is not disposed at the boundary part, oil drops or water drops in a measuring object gas adhere to the boundary part. As a result, thermal shock is imparted due to a difference in thermal shrinkage between mutual layers and a crack sometimes occurs in the layer. On the other hand, the cracking described above can be suppressed by thickening of a protective layer. However, this results in an increase in volume with an increase in the thickness of the protective layer. Consequently, a long activation time is required to heat the sensor element to a predetermined (activation) temperature at which the solid electrolyte is activated. Namely, the longer activation temperature becomes a factor in inhibiting speedy startup of a gas sensor.

SUMMARY OF THE INVENTION

It is therefore an object of the present invention to solve the above noted problems of the related art, and to suppress the occurrence of cracking due to thermal shock at a boundary part while limiting an increase in volume by an increase in the thickness of a protective layer in a laminated gas sensor element.

According to a first aspect (1), the above object of the present invention is achieved by providing a laminated gas sensor element extending in a longitudinal direction and having a detection part for detecting a specific gas in a leading end side of the laminated gas sensor element, comprising: a long plate-shaped element body including a heater layer having an embedded resistance heating body and a detection layer having a pair of electrodes laminated to the heater layer, the detection layer having a vertical surface along a lamination direction and a horizontal surface perpendicular to the lamination direction; and a porous protective layer coating the vertical surface and the horizontal surface of the element body constituting the detection part, wherein a thickness (t1) of the protective layer formed on the vertical surface is thicker than a thickness (t2) of the protective layer formed on the horizontal surface.

In the laminated gas sensor element (1) according to the first aspect, a protective layer coating a vertical surface having an exposed boundary part susceptible to cracking due to thermal shock is made thicker than a protective layer coating a horizontal surface. In this manner, water drops penetrate through the pores of the thicker protective layer coating the vertical surface more slowly than through the thinner protective layer coating the horizontal surface, so that a temperature gradient occurring in the vertical surface can be decreased and thermal shock can be suppressed. Moreover, the thickness of the protective layer of the horizontal surface is made thinner than that of the vertical surface and thereby, an increase in volume by an increase in the protective layer can be suppressed and the time needed to reach an activation temperature can be reduced.

As used herein, "vertical surface" means four surfaces along a lamination direction of the long plate-shaped element body, the "horizontal surface" means two surfaces along a direction perpendicular to the lamination direction of the long plate-shaped element body.

In a preferred embodiment (2), in the laminated gas sensor element according to the first aspect (1), the element body has a corner (ep) connecting the vertical surface to the horizontal surface, the corner part of the detection part is coated with the protective layer, and a thickness (t3) of the protective layer formed on the corner part is thinner than the thickness (t1) of the protective layer formed on the vertical surface and is thicker than the thickness (t2) of the protective layer formed on the horizontal surface. In this embodiment, the thickness of the protective layer at the corner part in which cracking due to thermal shock tends to occur more so than in the horizontal surface is made thicker than the protective layer of the horizontal surface. In this manner, thermal shock imparted to the corner part can also be suppressed. Moreover, the corner part resists cracking due to thermal shock more so than the vertical surface having an exposed boundary part, so that the protective layer at the corner part is made thinner than the protective layer of the vertical surface. Thus, an increase in volume due to an increase in thickness of the protective layer can be suppressed, and the time needed to reach the activation temperature can also be reduced.

As used herein, "thickness of the protective layer formed on the corner part" means a diameter of a virtual circle inscribed between a surface of the protective layer and the corner part of the element body in the case of taking a cross section of a lamination direction of the element body. Also, "corner part" means the portion connecting the vertical surface to the horizontal surface. The "corner part" is not limited to a linear part (that is, an edge) at which two surfaces intersect, and also includes a portion having a curved surface shape in which two surfaces are joined, for example, in an R shape.

In another preferred embodiment (3), in the laminated gas sensor element according to (1) or (2) above, the thickness (t1) of the protective layer coating the vertical surface (vf) of the element body is in a range of 300 μm to 500 μm and the thickness (t2) of the protective layer coating the horizontal surface (hf) of the element body is coated is in a range of 150 μm to 250 μm. In this embodiment, in the protective layer of the vertical surface, water drops can slowly penetrate while dispersing inside the pores of the protective layer, so that thermal shock imparted to the vertical surface can be suppressed. Also, thermal shock imparted to the horizontal surface can be suppressed while suppressing an increase in volume. In addition, when the thickness of the protective layer coating the vertical surface of the element is less than 300 μm, there are cases where thermal shock imparted to the vertical surface cannot be adequately suppressed. Also, when the thickness is greater than 500 μm, there are cases where the activation time is delayed due to an increase in volume. On the other hand, when the thickness of the protective layer coating the horizontal surface of the element is less than 150 μm, there are cases where the thermal shock imparted to the horizontal surface cannot be adequately suppressed.

In a preferred embodiment (4), in the laminated gas sensor element according to (1) or (2) above, the element body has a non-porous part and a porous part exposed at the horizontal surface of the detection part, wherein a thickness (t4) of the protective layer coating the porous part is thicker than the thickness (t2) of the protective layer coating the non-porous part, and the protective layer having the thickness (t4) coating the porous part is disposed so as to straddle a boundary between the porous part and the non-porous part. When the porous part and the non-porous part are disposed on the horizontal surface, cracking due to thermal shock tends to occur in the porous part or at a boundary part between the porous part and the non-porous part. However, since the protective layer coating the porous part or the boundary part is made thicker than the protective layer of the non-porous par, water drops penetrate more slowly while dispersing inside the pores of the thicker protective layer than in the thinner protective layer of the non-porous part. Consequently a temperature gradient occurring in the porous part or the boundary part can be decreased and thermal shock can be suppressed.

In yet another preferred embodiment (5) in the laminated gas sensor element according to (4) above, the thickness (t4) of the protective layer coating the porous part of the element body and the thickness (t1) of the protective layer coating the vertical surface (vf) of the element body are in a range of 300 μm to 500 μm. Also, the thickness (t2) of the protective layer coating the non-porous part of the element body is in a range of 150 μm to 250 μm. In this embodiment, in the protective layer of the vertical surface, water drops penetrate slowly while dispersing inside the pores of the thicker protective layer, so that thermal shock imparted to the vertical surface can be suppressed. Also, in the horizontal surface, thermal shock can be suppressed while suppressing an increase in volume. In addition, when thickness of the protective layer coating the porous part and the vertical surface of the element body is less than 300 μm, there are cases where thermal shock imparted to the vertical surface cannot be adequately suppressed. Also, when the thickness is greater than 500 μm, there are cases where the activation time is delayed by an increase in volume. On the other hand, when the thickness of the protective layer coating the non-porous part of the element body is less than 150 μm, there are cases where thermal shock imparted to the horizontal surface cannot be adequately suppressed.

In yet another preferred embodiment (6), in the laminated gas sensor element according to any one of (1) to (5) above, the protective layer comprises a first layer coating the vertical surface (vf) and a second layer having a porosity higher than that of the first protective layer, the second protective layer coating the first protective layer and the horizontal surface (hf). In this case, the first protective layer having a porosity lower than that of the second protective layer coating the horizontal surface is used to coat the vertical surface. In this manner, water drops penetrate through the pores of the first protective layer more slowly than through the second protective layer, so that a temperature gradient occurring in the vertical surface can be decreased and thermal shock can be further suppressed.

In yet another preferred embodiment (7), in the laminated gas sensor element according to (6) above, the thickness (t2a) of the second protective layer coating the first protective layer is equal to the thickness (t1a) of the second protective layer which coats the horizontal surface (hf). In this embodiment, the occurrence of cracking due to thermal shock can be suppressed easily by the second protective layer of uniform thickness.

In yet another preferred embodiment (8), in the laminated gas sensor element according to (6) or (7) above, the porosity of the first protective layer is in a range of 30% to 40% and the porosity of the second protective layer is in a range of 40% to 60%. In this embodiment, water drops penetrate through the pores of the first protective layer more slowly than through the second protective layer, so that thermal shock can be suppressed. In addition, when the porosity of the first protective layer is less than 30%, there are cases where the first protective layer becomes resistant to a measured gas passing therethrough, and the gas cannot be detected with high accuracy. Also, when the porosity of the first protective layer is greater than 40%, there are cases where water drops tend to pass through the protective layer and thermal shock imparted to the horizontal surface cannot be adequately suppressed. Further, when the porosity of the second protective layer is more than 60%, there are cases where water drops tend to pass through the protective layer and thermal shock imparted to the vertical surface cannot be adequately suppressed. Porosity in accordance with this invention is measured by the technique described in U.S. Pat. No. 7,329,844 incorporated herein by reference.

According to a second aspect (9), the above object of the invention is achieved by providing a laminated gas sensor element extending in a longitudinal direction and having a detection part for detecting a specific gas in a leading end side of the laminated gas sensor element, comprising: a long plate-shaped element body including a heater layer having an embedded resistance heating body and a detection layer having a pair of electrodes laminated to the heater layer, the detection layer having a vertical surface (hf) along a lamination direction and a horizontal surface (hf) perpendicular to the lamination direction; and a porous protective layer coating the vertical surface (vf) and the horizontal surface (hf) of that portion of the element body constituting the detection part, wherein the protective layer comprises a first protective layer coating the vertical surface, and a second protective layer having a porosity higher than that of the first protective layer coating the horizontal surface (hf).

In the laminated gas sensor element (9) according to the second aspect, a first protective layer having a porosity lower than that of a second protective layer coating the horizontal surface is used to coat the vertical surface having an exposed boundary part susceptible to cracking due to thermal shock. Thereby, water drops penetrate through the pores of the resistant first protective layer more slowly than through the protective layer of the horizontal surface. As a result, a temperature gradient occurring in the vertical surface can be decreased and thermal shock can be suppressed.

In a preferred embodiment (10), in the laminated gas sensor element (9) according to the second aspect, the element body has a non-porous part and a porous part exposed at the horizontal surface (hf) of the detection part, and the top of the porous part is coated with a third protective layer having a porosity equal to that of the first protective layer, and wherein the third protective layer is disposed so as to straddle a boundary between the porous part and the non-porous part. When the porous part and the non-porous part are disposed on the horizontal surface, cracking due to thermal shock tends to occur in the porous part or at a boundary between the porous part and the non-porous part. However, because the third protective layer having a porosity lower than that of a second protective layer is disposed so as to straddle the boundary part, water drops penetrate through the pores of the third protective layer more slowly than through the second protective layer, such that thermal shock can be suppressed.

In yet another preferred embodiment (11) in the laminated gas sensor element according to (9) or (10) of the second aspect, the porosities of the first protective layer and the third protective layer are in a range of 30% to 40%, and the porosity of the second protective layer is in a range of 40% to 60%. In this case, water drops penetrate through the pores of the resistant first or third protective layers more slowly than through the second protective layer, so that thermal shock can be suppressed. In addition, when the porosity of the first protective layer or the third protective layer is less than 30%, there are cases where these layers become resistant to a measured gas passing therethrough, and the gas cannot be detected with high accuracy. Also, when the porosity of the first protective layer or the third protective layer is greater than 40%, there are cases where water drops tend to pass through the protective layer and thermal shock in a horizontal surface cannot be suppressed. Further, when the porosity of the second protective layer is more than 60%, there are cases where water drops tend to pass through the protective layer and thermal shock imparted to the vertical surface cannot be adequately suppressed.

In yet another preferred embodiment (12), in the laminated gas sensor element according to (9) or (10) of the second aspect, the first protective layer, the second protective layer and the third protective layer each has a thickness in a range of 150 μm to 250 μm. In this case, in the protective layers, water drops penetrate slowly while dispersing inside the pores of the respective layers, such that thermal shock can be suppressed.

The invention can be implemented in various aspects other than those described above, and can be implemented, for example, in the form of a gas sensor comprising a gas sensor element body for detecting a measuring object gas formed in a long plate shape by laminating a base material having an embedded resistance heating body and a detection layer having a pair of electrodes, and a housing for supporting the gas sensor element body.

BRIEF DESCRIPTION OF THE DRAWINGS

Illustrative aspects of the invention will be described in detail with reference to the following figures, in which.

DETAILED DESCRIPTION OF THE PREFERRED EMBODIMENTS

A laminated gas sensor element according to the invention and a configuration of an air-fuel ratio sensor which is a gas sensor incorporating the laminated gas sensor element will hereinafter be described based on exemplary embodiments with reference to the drawings. However, the present invention should not be construed as being limited thereto.

A. First Exemplary Embodiment

A1. Configuration of Air-Fuel Ratio Sensor

Figure 1:
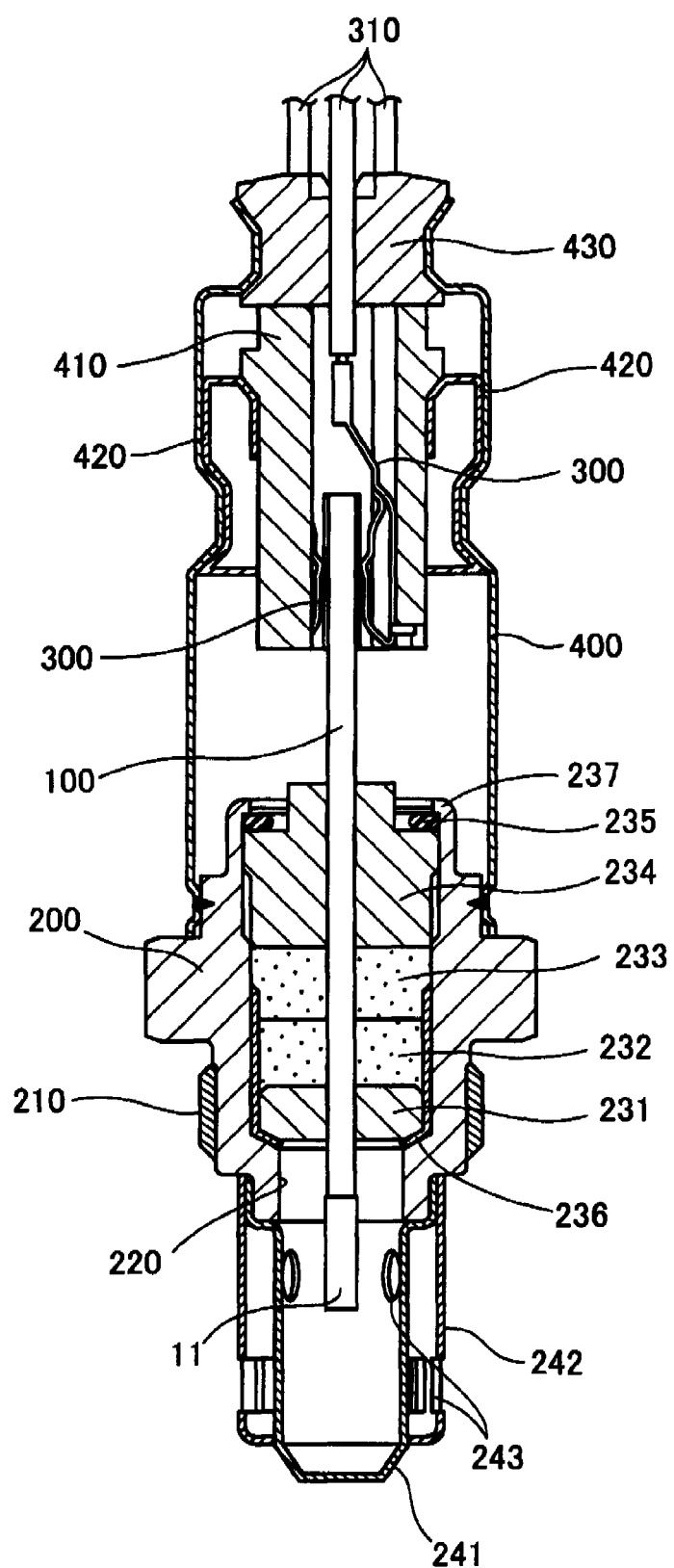
FIG. 1 is an explanatory diagram showing a configuration of an air-fuel ratio sensor 10 according to a first exemplary embodiment of the present invention.

FIG. 1 is an explanatory diagram showing the configuration of an air-fuel ratio sensor 10 as a first exemplary embodiment of the invention. The air-fuel ratio sensor 10 is attached to an exhaust pipe of various internal combustion engines or an automobile, and detects a specific gas component in exhaust gas (measuring object gas). The air-fuel ratio sensor 10 is used for performing air-fuel ratio feedback control in various internal combustion engines by detecting the specific gas. The air-fuel ratio sensor 10 comprises a gas sensor element 100, a metal shell 200, a connecting terminal 300 and an outer tube 400. The gas sensor element 100 will be described in detail below.

In addition, in the first exemplary embodiment, description is made by setting the lower side of the paper plane of FIG. 1 at the "leading end side" and setting the upper side of the paper plane of FIG. 1 at the "rear end side".

The metal shell 200 supports the gas sensor element 100 and protects the gas sensor element 100 from external shock and fixes the gas sensor element 100 in a predetermined position. The metal shell 200 has a tubular shape and a screw part 210, used for fixing to the exhaust pipe of the internal combustion engine, is formed in an outer surface. Also, the metal shell 200 further comprises a mouth part 220 whose inside diameter is smallest in the metal shell 200 in the leading end side beyond the screw part 210. The gas sensor element 100 is arranged through the inside of a tube of the metal shell 200 with a detection part 11 described below protruding beyond the mouth part 220. In addition, the metal shell 200 corresponds to a "housing" as claimed herein.

In order to position the gas sensor element 100, an annular ceramic holder 231, a first filling powder 232, a second filling powder 233 and a ceramic sleeve 234 are laminated between the metal shell 200 and the gas sensor element 100 sequentially from the leading end side. Further, a packing 235 is arranged between the ceramic sleeve 234 and the metal shell 200, and a metal holder 236 is arranged between the ceramic holder 231 and the metal shell 200. In the rear end 237 of the metal shell 200, the ceramic sleeve 234 is crimped via the packing 235.

An internal protector 241 with which the detection part 11 of the gas sensor element 100 is covered and an external protector 242 with which at least a part of the outer surface of the internal protector 241 is covered are bonded to the mouth part 220 of the metal shell 200 by welding, etc. The internal protector 241 and the external protector 242 are formed from a metal such as stainless steel comprising plural hole parts 243. A measuring object gas is introduced from the hole parts 243 of the internal protector 241 and the external protector 242 to the inside of the protector so as to make contact with the gas sensor element 100. Also, a situation in which water drops or solids make direct contact with the gas sensor element 100 is reduced by shifting positions of the hole parts in the internal protector 241 and the external protector 242.

The connecting terminal 300 is electrically connected to a first electrode terminal part 119c, a second electrode terminal part 119d, a third electrode terminal part 119e and heater side electrode terminal parts 124 of the gas sensor element 100 described below. The connecting terminal 300 is connected to lead wires 310, and the connecting terminal 300 transmits an electrical signal generated by the gas sensor element 100 with detection of gas to a controller (not shown) through the lead wires 310.

The outer tube 400 has a tubular shape. The leading end portion is fixed to an outer surface of the metal shell 200, and the portion of connection between the gas sensor element 100 and the connecting terminal 300 is covered with the outer tube 400. A tube-shaped insulating contact member 410 is arranged inside the outer tube, and connection between the connecting terminal 300 and the gas sensor element 100 is made inside the insulating contact member 410. An annular holding member 420 is present between the insulating contact member 410 and the outer tube 400, and the insulating contact member 410 is fixed inside the outer tube 400 by the holding member 420. A grommet 430 for sealing an opening of the outer tube 400 is arranged in the rear end side of the outer tube 400. The lead wires 310 are connected to the controller through the grommet 430.

A2. Configuration of Gas Sensor Element

Figure 2:
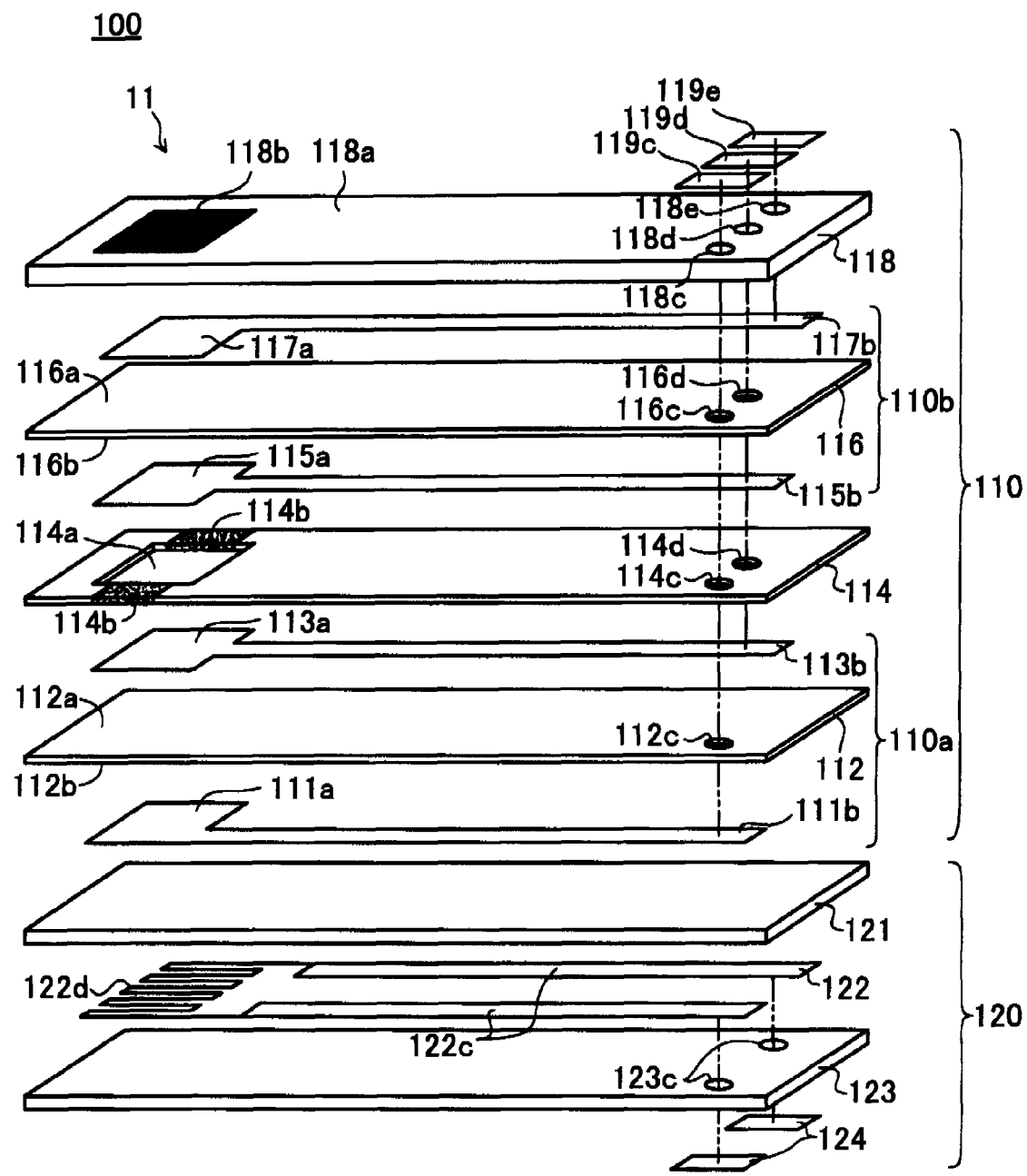
FIG. 2 is an explanatory diagram showing a configuration of a gas sensor element 100 according to a first exemplary embodiment of the present invention.

FIG. 2 is an explanatory diagram showing a configuration of the gas sensor element 100 as the first exemplary embodiment. The gas sensor element 100 is formed in a long plate shape by laminating a detection element 110 and a heater 120. In addition, in FIG. 2, the detection element 110 in the gas sensor element 100 is represented as the "upper side" and the heater 120 is represented as the "lower side". Also, the left side of the paper plane in FIG. 2 is represented as the "leading end side" and the right side of the paper plane is represented as the "rear end side". The detection element 110 is formed by laminating an oxygen concentration detection cell 110a and an oxygen pump cell 110b so that the oxygen pump cell 110b is located in the upper side, and the detection part 11 is formed in the leading end side. The gas sensor element 100 corresponds to an element body as claimed herein and the detection element 110 corresponds to a detection layer and the heater 120 corresponds to a heater layer.

The oxygen concentration detection cell 110a comprises a first solid electrolyte layer 112, a first electrode 111a and a second electrode 113a. The first electrode 111a is arranged so as to oppose the second electrode 113a through the leading end side of the first solid electrolyte layer 112. The rear end side of the first solid electrolyte layer 112 comprises a first through hole 112c. Also, the first electrode 111a is arranged in a back surface 112b (lower side) of the first solid electrolyte layer 112 so as to be covered with a first substrate 121 described below. On the other hand, the second electrode 113a is arranged in a front surface 112a (upper side) of the first solid electrolyte layer 112 so as to be exposed to a measuring chamber 114a described below. In addition, the first electrode 111a and the second electrode 113a are respectively connected to a first lead part 111b and a second lead part 113b extending toward the rear end side. The oxygen concentration detection cell 110a generates a voltage according to a difference between oxygen concentrations in the first electrode 111a and the second electrode 113a as an oxygen concentration battery element.

The oxygen pump cell 110b comprises a second solid electrolyte layer 116, a third electrode 115a and a fourth electrode 117a. The third electrode 115a is arranged so as to oppose the fourth electrode 117a through the leading end side of the second solid electrolyte layer 116. The rear end side of the second solid electrolyte layer 116 comprises a fourth through hole 116c and a fifth through hole 116d. Also, the third electrode 115a is arranged in a back surface 116b (lower side) of the second solid electrolyte layer 116 so as to be exposed to the measuring chamber 114a described below. On the other hand, the fourth electrode 117a is arranged in a front surface 116a (upper side) of the second solid electrolyte layer 116 so as to be covered with a porous part 118b described below. In addition, the third electrode 115a and the fourth electrode 117a are respectively connected to a third lead part 115b and a fourth lead part 117b extending toward the rear end side. The oxygen pump cell 110b moves oxygen inside the second solid electrolyte layer 116 when a potential difference is applied between the fourth electrode 117a and the third electrode 115a. Concretely, the oxygen pump cell 110b pumps oxygen into and out of the measuring chamber 114a by moving the oxygen so that electromotive force generated by the oxygen concentration detection cell 110a becomes constant (for example, 450 mV). Then, the detection element 110 outputs air-fuel ratio information using a value (current value) of a current required for the oxygen pump cell 110b to pump oxygen into and out of the measuring chamber 114a as an index.

The first solid electrolyte layer 112 and the second solid electrolyte layer 116 are fabricated from a partially-stabilized zirconia sintered body made by adding yttria ($Y_2O_3$) or calcia (CaO) to zirconia ($ZrO_2$) as a stabilizing agent.

Also, the first electrode 111a, the second electrode 113a, the third electrode 115a, the fourth electrode 117a, the first lead part 111b, the second lead part 113b, the third lead part 115b and the fourth lead part 117b can be respectively formed of platinum group elements, preferably Pt, Rh or Pd. Further, each of the electrodes 111a, 113a, 115a, 117a and each of the lead parts 111b, 113b, 115b, 117b described above may be formed of one kind of material or may be formed of two or more kinds of materials.

Further, the detection element 110 is made by laminating the oxygen concentration detection cell 110a and the oxygen pump cell 110b through an insulating layer 114 and also by disposing a protective layer 118 on an upper surface of the oxygen pump cell 110b.

The insulating layer 114 comprises the measuring chamber 114a arranged between the first solid electrolyte layer 112 and the second solid electrolyte layer 116, and further comprises a diffusion-limited layer 114b for diffusing and limiting a measuring object gas from outside of the gas sensor element 100 and allowing the measuring object gas to flow into the measuring chamber 114a. Further, the rear end of the insulating layer 114 comprises a second through hole 114c and a third through hole 114d. The insulating layer 114 is not particularly limited as long as the layer is a ceramic sintered body having insulation properties, and can be formed of oxide system ceramics such as alumina or mullite. Also, the diffusion-limited layer 114b is not particularly limited as long as the layer is a porous body, and can be formed of a porous body made of, for example, alumina.

The protective layer 118 comprises a body part 118a, a porous part 118b, a sixth through hole 118c, a seventh through hole 118d and an eighth through hole 118e. The porous part 118b is arranged in a hole part disposed in the body part 118a of an upper surface of the fourth electrode 117a, through which the gas outside of the gas sensor element 100 can make contact with the fourth electrode 117a. The sixth through hole 118c, the seventh through hole 118d and the eighth through hole 118e are arranged in the rear end of the body part 118a of the protective layer 118, and a first electrode terminal part 119c, a second electrode terminal part 119d and a third electrode terminal part 119e are arranged on upper surfaces of each of the through holes so as to cover each of the through holes. The electrode terminal parts 119c, 119d and 119e described above can be formed of platinum group elements, preferably Pt, Rh or Pd. The electrode terminal parts 119c, 119d and 119e described above may be formed of one kind of material or may be formed of two or more kinds of materials.

In addition, the first lead part 111b is connected to the first electrode terminal part 119c through the first through hole 112c, the second through hole 114c, the fourth through hole 116c and the sixth through hole 118c. Also, the second lead part 113b is connected to the second electrode terminal part 119d through the third through hole 114d, the fifth through hole 116d and the seventh through hole 118d. The third lead part 115b is connected to the second electrode terminal part 119d through the fifth through hole 116d and the seventh through hole 118d. The fourth lead part 117b is connected to the third electrode terminal part 119e through the eighth through hole 118e.

The heater 120 comprises a first substrate 121, a second substrate 123 and a resistance heating body 122. The first substrate 121 and the second substrate 123 are formed of plate-shaped members using alumina as a main body so as to sandwich the resistance heating body 122 with the first substrate 121 turned to the upper side. The rear end side of the second substrate 123 comprises heater side through holes 123c, and the lower surfaces of the heater side through holes 123c comprise heater side electrode terminal parts 124. The resistance heating body 122 comprises a heating part 122d arranged in the top end, and a pair of heater lead parts 122c extending from the heating part 122d to the rear end side of the gas sensor element 100. The heater lead parts 122c are connected to the heater side electrode terminal parts 124 through the heater side through holes 123c disposed in the second substrate 123.

The resistance heating body 122 and the heater side electrode terminal parts 124 can be formed of platinum group elements, preferably Pt, Rh or Pd. The resistance heating body 122 and the heater side electrode terminal parts 124 may be formed of one kind of material or may be formed of two or more kinds of materials.

In addition, the first electrode 111a, the second electrode 113a, the third electrode 115a, the fourth electrode 117a, the first lead part 111b, the second lead part 113b, the third lead part 115b and the fourth lead part 117b, the first electrode terminal part 119c, the second electrode terminal part 119d and the third electrode terminal part 119e, the resistance heating body 122 and the heater side electrode terminal parts 124 are preferably formed of Pt as a main component so as to provide heat resistance and oxidation resistance. Further, a ceramic component is preferably added in addition to the main component platinum group elements. The ceramic component is preferably a component similar to a material (for example, a material used as a main body of the first solid electrolyte layer 112, the second solid electrolyte layer 116, the body part 118a of the protective layer 118, the second substrate 123) used as a main body of the laminated side so as to impart good fixing properties.

A3. Coating of Gas Sensor Element

Figure 3:
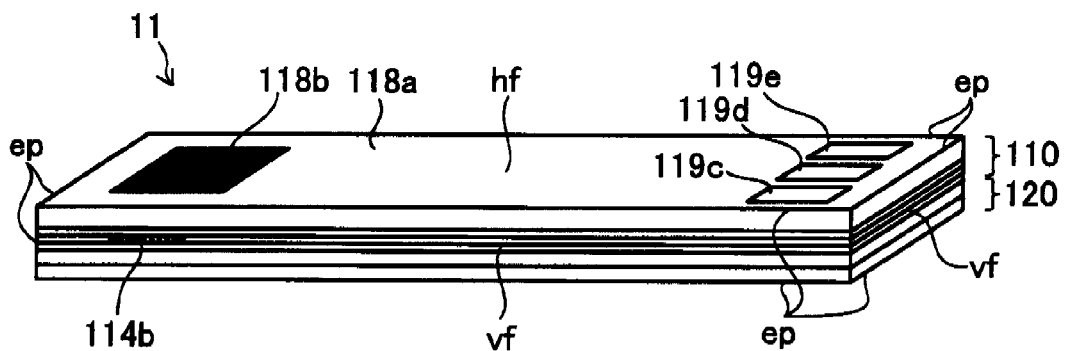
FIG. 3 is an illustrative diagram showing an external appearance of a gas sensor element.

FIG. 3 is an illustrative diagram showing an external appearance of the gas sensor element. An outer surface of the gas sensor element 100 comprises a vertical surface vf, a horizontal surface hf and a corner part ep. The vertical surface vf is a surface along a lamination direction of laminating the detection element 110 and the heater 120 among the components of the gas sensor element 100. The horizontal surface hf is the uppermost surface of the detection element 110 and the lowest surface of the heater 120 among the components of the gas sensor element 100. The corner part ep connects the vertical surface and the horizontal surface and is formed in a line shape or a surface shape. The leading end side of the gas sensor element 100 functions as the detection part 11 for introducing a measuring object gas into the measuring chamber 114a through the diffusion-limited layer 114b and detecting a specific gas such as oxygen.

Figure 4:
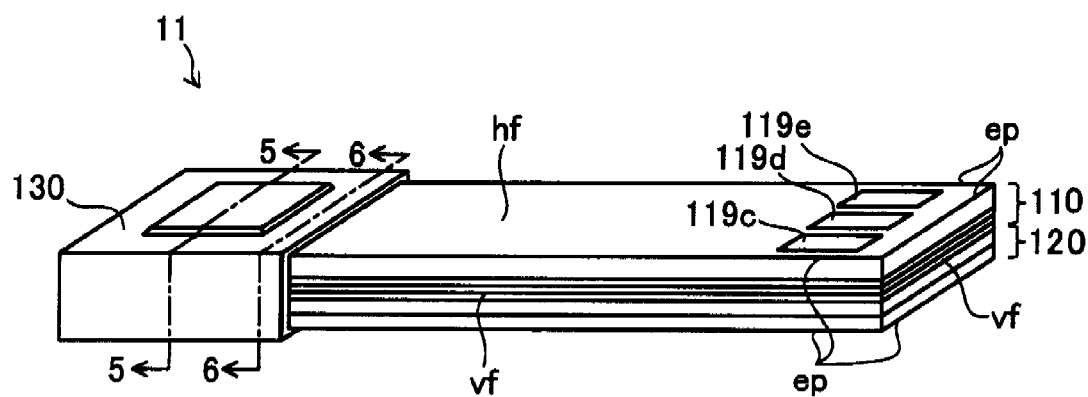
FIG. 4 is an illustrative diagram showing the external appearance of the gas sensor element having a coated detection part 11.

In operation, the detection part 11 is heated by the heater 120 and is in a high temperature state of 300° C. or more. As a result, when oil drops or water drops in a measuring object gas adhere, a crack may occur due to thermal shock. On the other hand, in the gas sensor element 100, the vertical surface vf, the horizontal surface hf and the corner part ep in the vicinity of the detection part 11 are coated with a coating part 130. FIG. 4 is an illustrative diagram showing an external appearance of the gas sensor element in which the detection part 11 is coated. In addition, the coating part 130 corresponds to a protective layer as claimed herein.

The coating part 130 is formed by making a slurry made of spinel powder, titania powder and alumina sol. The slurry is applied to the vicinity of the detection part of the gas sensor element 100 and heat treated at a calcination temperature of 1000° C. for 3 hours (calcination time). In applying the slurry, a spray, etc., may be used to form the coating.

Figure 5:
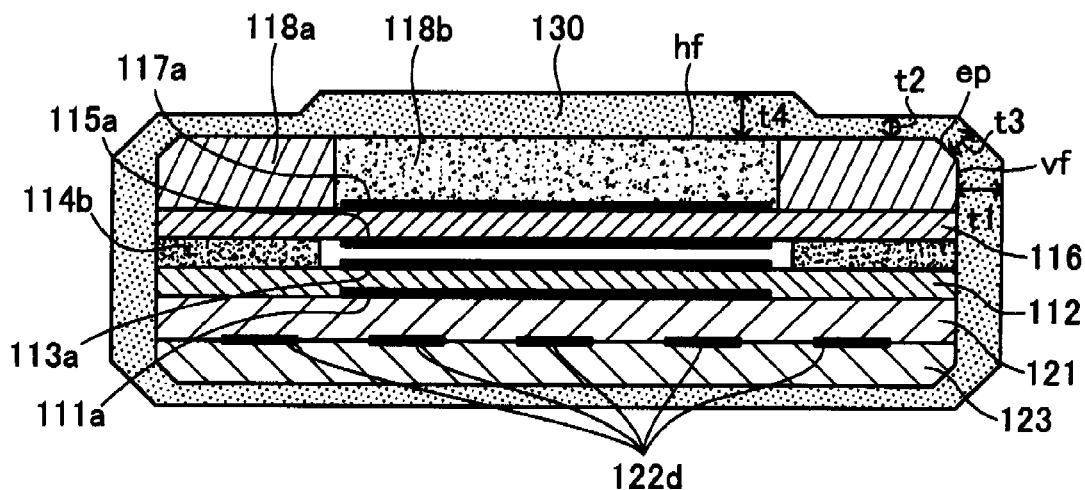
FIG. 5 is an explanatory diagram illustrating a cross sectional view along line 5-5 of FIG. 4.
Figure 6:
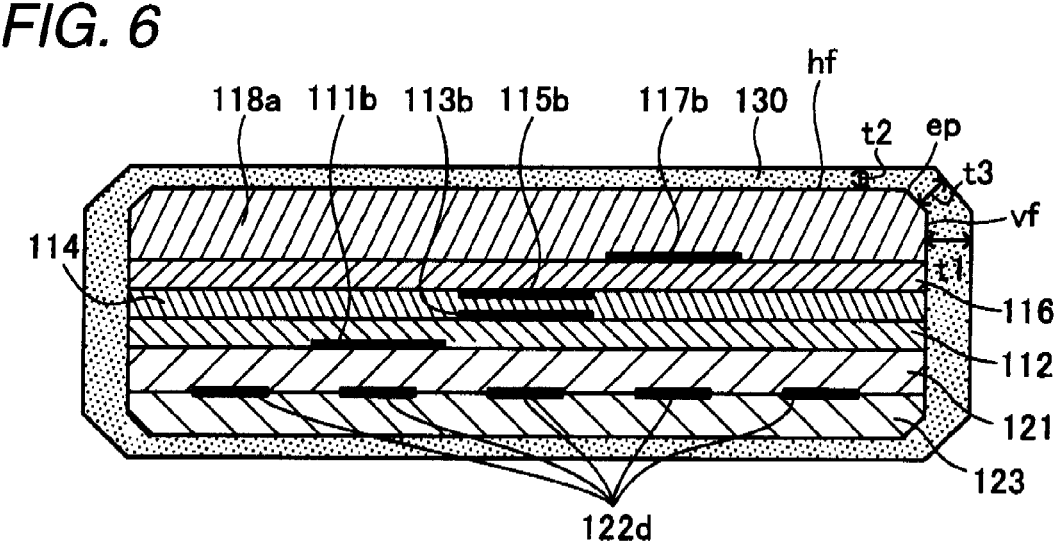
FIG. 6 is an explanatory diagram illustrating a cross sectional view along line 6-6 of FIG. 4.

FIG. 5 is an explanatory diagram illustrating a cross sectional view along 5-5 of FIG. 4. FIG. 6 is an explanatory diagram illustrating a cross sectional view along 6-6 of FIG. 4. The coating part 130 is formed so that a coating thickness t1 on the vertical surface vf becomes thicker than a coating thickness t2 on the horizontal surface hf. Also, the coating part 130 is formed so that a coating thickness t3 on the corner part ep becomes thinner than t1 and becomes thicker than t2. Further, the coating part 130 is formed so that a coating thickness t4 on the porous part 118b becomes thicker than the coating thickness t2 on the horizontal surface hf and further, the coating part 130 of the coating thickness t4 is formed so as to straddle a boundary between the porous part 118b and the body part 118a. For example, coating parts having different coating thicknesses are formed by changing number of times of coating the slurry on the gas sensor element. Further, coating parts having different coating thicknesses are formed by changing a time for spraying.

The coating thickness t1 on the vertical surface vf of the coating part 130 is in a range of 300 μm to 500 μm. The coating thickness t2 on the horizontal surface hf of the coating part 130 is in a range of 150 μm to 250 μm. The coating thickness t3 on the corner part ep of the coating part 130 is in a range of 150 μm to 500 μm. The coating thickness t4 in the vicinity of an upper surface of the porous part 118b of the coating part 130 is in a range of 300 μm to 500 μm. In addition, a porosity of the coating part 130 is in a range of 40% to 60%.

According to the laminated gas sensor element of the first exemplary embodiment described above, the coating thickness t1 of the coating part 130 on the vertical surface vf in which cracking due to thermal shock tends to occur is made thicker than the coating thickness t2 on the horizontal surface hf. In this manner, water drops penetrate through the pores of the coating part on the vertical surface more slowly than through the coating part 130 on the horizontal surface hf. Further, a temperature gradient occurring in the vertical surface can be decreased and a thermal shock in the vertical surface vf can be further suppressed. Also, a thickness of the coating part 130 of the horizontal surface hf is made thinner than that of the vertical surface vf. Thereby, an increase in volume of the gas sensor element by the coating can be suppressed while suppressing thermal shock imparted to the horizontal surface hf. Also, an increase in time necessary to heat the detection part of the gas sensor element to an activation temperature can be suppressed.

Further, according to the laminated gas sensor element of the first exemplary embodiment, the coating thickness t3 of the coating part 130 on the corner part ep in which cracking due to thermal shock tends to occur is made thicker than the coating thickness t2 on the horizontal surface hf. In this manner, thermal shock imparted to the corner part ep can be further suppressed. Also, a thickness of the coating part 130 of the horizontal surface hf is made thinner than that of the corner part ep. Thereby, an increase in volume of the gas sensor element can be suppressed while suppressing thermal shock imparted to the horizontal surface hf.

According to the laminated gas sensor element of the first exemplary embodiment, the coating thickness t4 of the coating part 130 on the porous part 118b is made thicker than the coating thickness t2 on the horizontal surface hf. Further, a boundary between the porous part 118b and the body part 118a is covered with the coating part 130 of coating thickness t4. Thereby, thermal shock imparted to the porous part 118b or at the boundary between the porous part 118b and the body part 118a can be further suppressed. Also, a thickness of the coating part 130 of the horizontal surface hf of the body part 118a is made thinner than that of the porous part 118b. Thereby, an increase in volume of the gas sensor element can be suppressed while suppressing thermal shock imparted to the horizontal surface hf.

B. Second Exemplary Embodiment

A gas sensor element 100 in which a coating thickness in the vicinity of a detection part is changed using coating parts having different porosities will be described in a second exemplary embodiment. The external appearance of the gas sensor element 100 according to the second exemplary embodiment is similar to that of the gas sensor element 100 shown in FIG. 4. In the second exemplary embodiment, components assigned the same reference numerals as those of the first exemplary embodiment have the same function. For example, coating parts having different porosities are formed by using material (slurry etc.) that has different particle diameters. Further, coating parts having different porosities are formed by changing contained amounts of sublimation material included in the material. Further, in case coating sensor element by spraying, coating parts having different porosities are formed by changing a time for spraying or by changing a distance between a spray and the gas sensor element.

Figure 7:
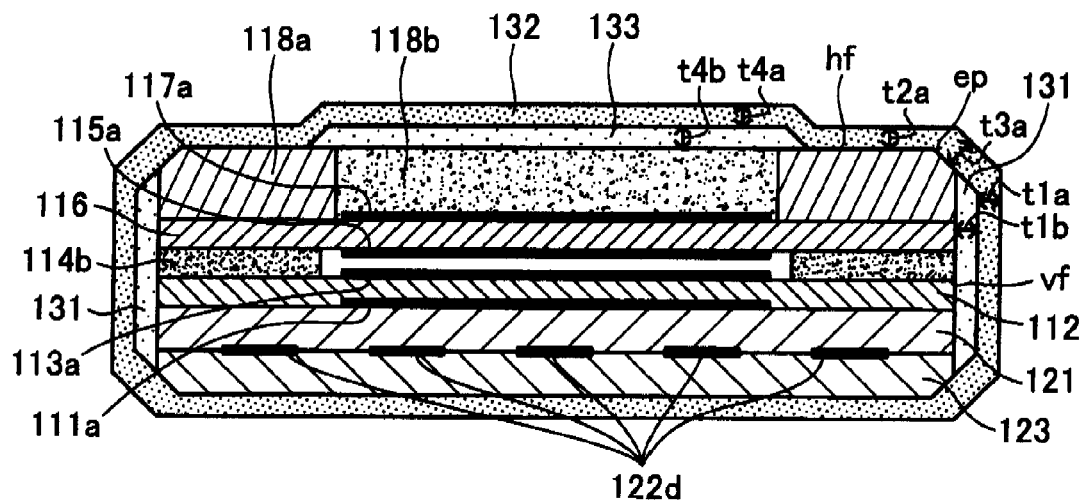
FIG. 7 is an explanatory diagram illustrating a cross sectional view along line 5-5 in a gas sensor element according to the second exemplary embodiment.
Figure 8:
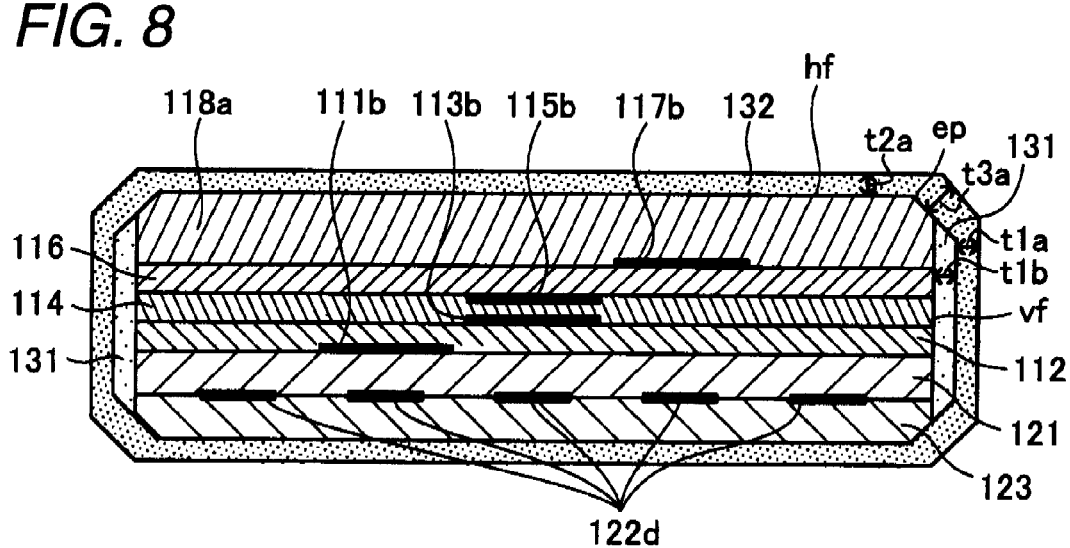
FIG. 8 is an explanatory diagram illustrating a cross sectional view along line 6-6 in the gas sensor element according to the second exemplary embodiment.

FIG. 7 is an explanatory diagram illustrating a cross sectional view along line 5-5 in the gas sensor element according to the second exemplary embodiment. FIG. 8 is an explanatory diagram illustrating a cross sectional view along line 6-6 in the gas sensor element according to the second exemplary embodiment. In the second exemplary embodiment, a coating part 130 is constructed by a first coating part 131, a second coating part 132 and a third coating part 133 having different porosities. In addition, the first coating part 131 and the third coating part 133 may have the same porosity. In the gas sensor element 100, a vertical surface vf in the vicinity of the detection part is coated with the first coating part 131. Also, in the gas sensor element 100, a porous part 118b is coated with the third coating part 133 and this third coating part 133 is disposed so as to straddle a boundary between a body part 118a and the porous part 118b. Further, in the gas sensor element 100, the first coating part 131, the third coating part 133, a corner part ep and a horizontal surface hf in the vicinity of the detection part are coated with the second coating part 132. The porosity of the second coating part 132 is in a range of 40% to 60% in a manner similar to the coating part 130 of the first embodiment. The first coating part 131 and the third coating part 133 are porous, and porosities of the first coating part 131 and the third coating part 133 are lower than that of the second coating part 132 and are in a range of 30% to 40%. In addition, in the second exemplary embodiment, the first coating part 131 corresponds to a first protective layer, the second coating part 132 corresponds to a second protective layer and the third coating part 133 corresponds to a third protective layer.

The second coating part 132 is formed so that a coating thickness t1a on the vertical surface vf, a coating thickness t2a on the horizontal surface hf and a coating thickness t4a on the porous part 118b each has the same thickness. Also, the second coating part 132 and the first coating part 131 are formed so that a total coating thickness t1b of the first coating part 131 and the coating thickness t1a of the second coating part 132 on the vertical surface vf becomes thicker than the coating thickness t2a of the second coating part 132 on the horizontal surface hf. Further, the second coating part 132 and the first coating part 131 are formed so that a coating thickness t3a of the second coating part 132 on the corner part ep becomes thinner than a total of the coating thickness t1b of the first coating part 131 and the coating thickness t1a of the second coating part 132 on the vertical surface vf and becomes thicker than the coating thickness t2a of the second coating part 132 on the horizontal surface hf. Further, the second coating part 132 and the third coating part 133 are formed so that a total of a coating thickness t4b of the third coating part 133 and the coating thickness t4a of the second coating part 132 on the porous part 118b becomes thicker than the coating thickness t2a of the second coating part 132 on the horizontal surface hf.

The coating thickness t1a on the vertical surface vf of the second coating part 132, a coating thickness t2a on the horizontal surface hf and the coating thickness t4a in the vicinity of an upper surface of the porous part 118b are in a range of 150 μm to 250 μm.

The total of the coating thickness t1b of the first coating part 131 and the coating thickness t1a of the second coating part 132 on the vertical surface vf is in a range of 300 μm to 500 μm. The coating thickness t3a on the corner part ep of the second coating part 132 is in a range of 150 μm to 500 μm. The total of the coating thickness t4b of the third coating part 133 and the coating thickness t4a of the second coating part 132 in the vicinity of an upper surface of the porous part 118b is in a range of 300 μm to 500 μm.

According to the laminated gas sensor element of the second exemplary embodiment as described above, in the gas sensor element 100, the vertical surface vf is coated with the first coating part 131 so that thermal shock imparted to the vertical surface vf can be suppressed. Further, according to the laminated gas sensor element of the second exemplary embodiment, in the gas sensor element 100, the porous part 118b is coated with the third coating part 133, and the third coating part 133 is formed so as to straddle the body part 118a and the porous part 118b. In this manner, thermal shock imparted to the porous part 118b and at the boundary between the porous part 118b and the body part 118a can be suppressed.

According to the laminated gas sensor element of the second exemplary embodiment, it is unnecessary to change the coating thicknesses in the first coating part 131 and the second coating part 132, so that formation is easy and the occurrence of cracking due thermal shock can be easily suppressed.

C. Third Exemplary Embodiment

A gas sensor element 100 in which the vicinity of a detection part is coated using coating parts having different porosities will be described in a third embodiment. An external appearance of the gas sensor element 100 according to the third exemplary embodiment is similar to that of the gas sensor element 100 shown in FIG. 4. In the third exemplary embodiment, components assigned the same reference numerals as those of the first and second exemplary embodiments have the same respective function.

Figure 9:
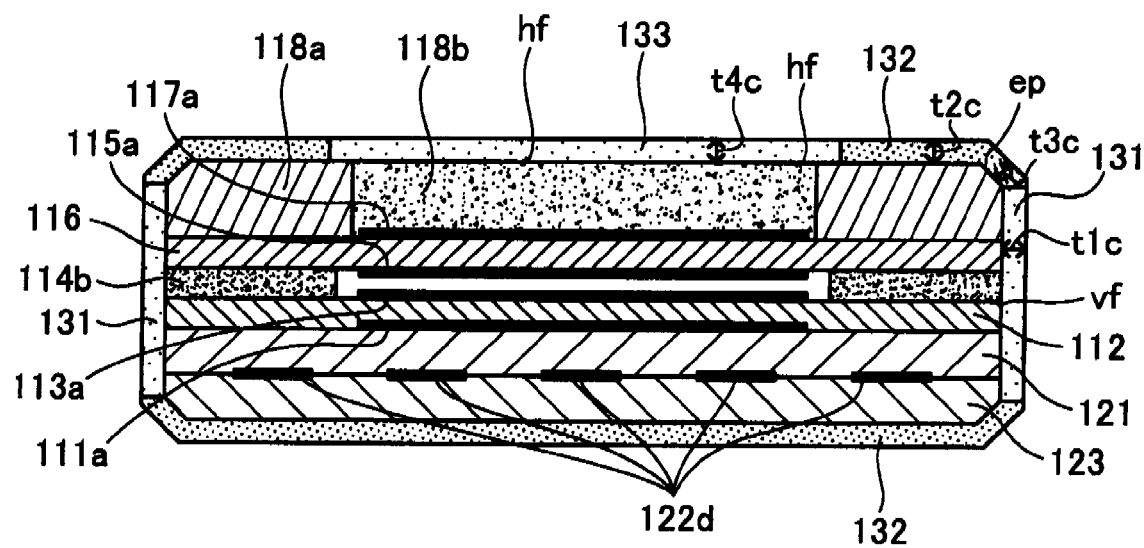
FIG. 9 is an explanatory diagram illustrating a cross sectional view along line 5-5 in a gas sensor element according to a third exemplary embodiment.
Figure 10:
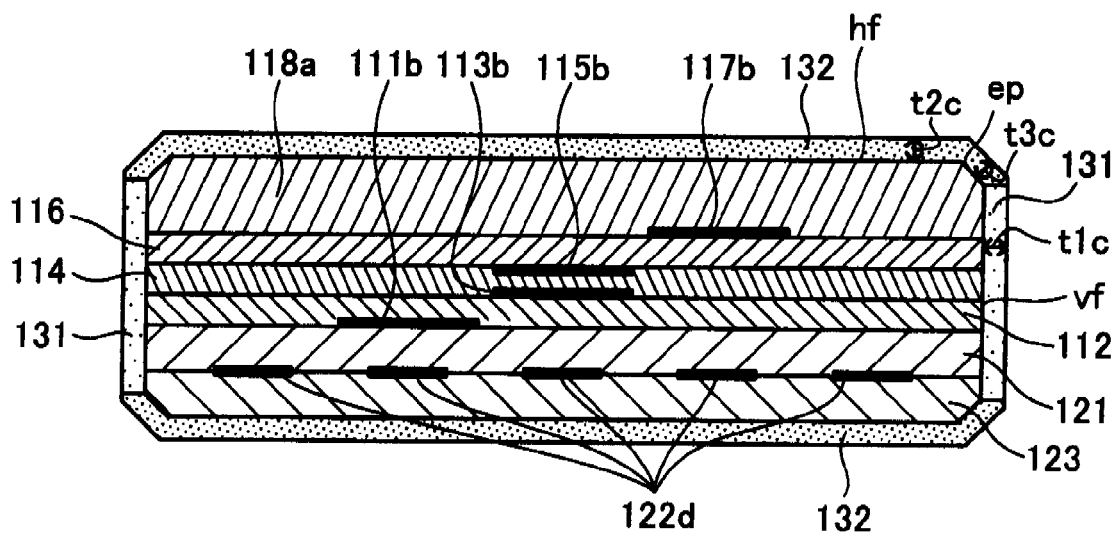
FIG. 10 is an explanatory diagram illustrating a cross sectional view along line 6-6 in the gas sensor element according to the third exemplary embodiment.

FIG. 9 is an explanatory diagram illustrating a cross sectional view along line 5-5 in the gas sensor element according to the third exemplary embodiment. FIG. 10 is an explanatory diagram illustrating a cross sectional view along line 6-6 in the gas sensor element according to the third exemplary embodiment. In the gas sensor element 100, a vertical surface vf in the vicinity of the detection part is coated with a first coating part 131. Also, in the gas sensor element 100, a porous part 118b is coated with a third coating part 133 and this third coating part 133 is formed so as to straddle a boundary between a body part 118a and the porous part 118b. Further, in the gas sensor element 100, a corner part ep and a horizontal surface hf in the vicinity of the detection part are coated with a second coating part 132.

The first coating part 131, the second coating part 132 and the third coating part 133 are formed so that each has the same thickness. The second coating part 132 is formed so that a coating thickness t2c on the horizontal surface hf and a coating thickness t3c on the corner part ep become the same. The first coating part 131 is formed so that a coating thickness t1c on the vertical surface vf becomes equal to the coating thickness t2c on the horizontal surface hf of the second coating part 132. Also, the third coating part 133 is formed so that a coating thickness t4c on the porous part 118b becomes equal to the coating thickness t2c on the horizontal surface hf of the second coating part 132. In addition, the coating thicknesses of the first coating part 131, the second coating part 132 and the third coating part 133 are in a range of 150 μm to 250 μm.

According to the laminated gas sensor element of the third exemplary embodiment described above, in the gas sensor element 100, a region in which cracking due to thermal shock tends to occur is coated with the first coating part 131 or the third coating part 133 having a porosity lower than that of the second coating part 132. As a result, thermal shock to the region in which cracking tends to occur can be further suppressed without changing the coating thickness. Also, the thermal shock imparted to each of the regions can be suppressed while suppressing an increase in volume of the gas sensor element.

D. MODIFIED EXAMPLE

The laminated gas sensor element can be implemented in various modified embodiments without departing from the gist of the invention.

D1. Modified Embodiment 1

In the first exemplary embodiment, the coating thicknesses t2 on the horizontal surface hf of the coating part 130 are equal in the uppermost surface of the detection element 110 and the lowermost surface of the heater 120, but the coating thicknesses may be different.

D2. Modified Embodiment 2

In the first exemplary embodiment, the coating part 130 is represented such that the coating thickness t1 on the vertical surface vf and the coating thickness t4 in the vicinity of the upper surface of the porous part 118b are the same, but the thicknesses may be different.

D3. Modified Embodiment 3

In the second exemplary embodiment, the vertical surface vf in the vicinity of the detection part is coated with the first coating part 131, and the entire vicinity of the upper surface of the porous part 118b is coated with the third coating part 133. However, only a part of the porous part 118b and the vertical surface vf in the vicinity of the detection part may be coated. For example, only the vicinity of a lamination interface which is a bonded surface of members of different kinds may be coated with the first coating part 131 and the other portion may be coated with the second coating part 132.

D4. Modified Embodiment 4

In the above exemplary embodiments, the corner part ep of the gas sensor element 100 is constructed as a surface, but may be a line constructed as a portion connecting the vertical surface vf and the horizontal surface hf. In this case, the coating thickness t3 on the corner part ep can be set, for example, as a coating thickness on a bisector of an angle between the vertical surface vf and the horizontal surface hf.

D5. Modified Embodiment 5

In the exemplary embodiments, the detection element 110 of the gas sensor element 100 is formed by laminating the oxygen concentration detection cell 110a and the oxygen pump cell 110b. However, the present invention is not limited thereto. For example, the detection element 110 may be constructed of an oxygen pump cell alone.

The invention can be implemented in various modes other than the embodiments and modified embodiments described above, and can be implemented, for example, as a method of manufacturing a laminated gas sensor element having an element body formed in a long plate shape by laminating a base material having an embedded resistance heating body and a detection layer having a pair of electrodes.

It should further be apparent to those skilled in the art that various changes in form and detail of the invention as shown and described above may be made. It is intended that such changes be included within the spirit and scope of the claims appended hereto.

This application is based on Japanese Patent Application No. 2008-104394 filed on Apr. 14, 2008, the disclosure of which is incorporated by reference herein in its entirety.

What is claimed is:

1. A laminated gas sensor element extending in a longitudinal direction and having a detection part for detecting a specific gas in a leading end side of the laminated gas sensor element, comprising:
    a plate-shaped element body including a heater layer having an embedded resistance heating body and a detection layer having a pair of electrodes laminated to the heater layer, the detection layer having a vertical surface (vf) along a lamination direction and a horizontal surface (hf) perpendicular to the lamination direction; and
    a porous protective layer coating the vertical surface and the horizontal surface of that portion of the element body constituting the detection part,
    wherein a thickness (t1) of the protective layer formed on the vertical surface is thicker than a thickness (t2) of the protective layer formed on the horizontal surface.

2. The laminated gas sensor element according to claim 1, wherein the element body has a corner part (ep) connecting the vertical surface to the horizontal surface, the corner part of the detection part is coated with the protective layer, and a thickness (t3) of the protective layer formed on the corner part is thinner than the thickness (t1) of the protective layer formed on the vertical surface and is thicker than the thickness (t2) of the protective layer formed on the horizontal surface.

3. The laminated gas sensor element according to claim 1, wherein the thickness (t1) of the protective layer coating the vertical surface (vf) of the element body is in a range of 300 μm to 500 μm and the thickness (t2) of the protective layer coating the horizontal surface (hf) of the element body is in a range of 150 μm to 250 μm.

4. The laminated gas sensor element according to claim 1, wherein the element body has a non-porous part and a porous part exposed at the horizontal surface of the detection part, and
    wherein a thickness (t4) of the protective layer coating the porous part is thicker than the thickness (t2) of the protective layer coating the non-porous part, and the protective layer having the thickness (t4) coating the porous part is disposed so as to straddle a boundary between the porous part and the non-porous part.

5. The laminated gas sensor element according to claim 4, wherein the thickness (t4) of the protective layer coating the porous part of the element body and the thickness (t1) of the protective layer coating the vertical surface (vf) of the element body are in a range of 300 μm to 500 μm, and
    wherein the thickness (t2) of the protective layer coating the non-porous part of the element body is in a range of 150 μm to 250 μm.

6. The laminated gas sensor element according to claim 1, wherein the protective layer comprises a first layer coating the vertical surface (vf) and a second layer having a porosity higher than that of the first protective layer, the second protective layer coating the first protective layer and the horizontal surface (hf).

7. The laminated gas sensor element according to claim 6, wherein the thickness (t2a) of the second protective layer coating the first protective layer is equal to the thickness (t1a) of the second protective layer which coats the horizontal surface (hf).

8. The laminated gas sensor element according to claim 6, wherein the porosity of the first protective layer is in a range of 30% to 40% and the porosity of the second protective layer is in a range of 40% to 60%.

9. A gas sensor comprising:
    a gas sensor element for detecting a measuring object gas; and
    a housing for supporting the gas sensor element,
    wherein the gas sensor element is the laminated gas sensor element as claimed in claim 1.

10. A laminated gas sensor element extending in a longitudinal direction and having a detection part for detecting a specific gas in a leading end side of the laminated gas sensor element, comprising:
    a plate-shaped element body including a heater layer having an embedded resistance heating body and a detection layer having a pair of electrodes laminated to the heater layer, the detection layer having a vertical surface (vf) along a lamination direction and a horizontal surface (hf) perpendicular to the lamination direction; and
    a porous protective layer coating the vertical surface (vf) and the horizontal surface (hf) of that portion of the element body constituting the detection part,
    wherein the protective layer comprises a first protective layer coating the vertical surface and a second protective layer having a porosity higher than that of the first protective layer coating the horizontal surface (hf).

11. The laminated gas sensor element according to claim 10, wherein the element body has a non-porous part and a porous part exposed at the horizontal surface (hf) of the detection part, and the top of the porous part is coated with a third protective layer having a porosity equal to that of the first protective layer, and
    wherein the third protective layer is disposed so as to straddle a boundary between the porous part and the non-porous part.

12. The laminated gas sensor element according to claim 11, wherein the porosities of the first protective layer and the third protective layer are in a range of 30% to 40% and the porosity of the second protective layer is in a range of 40% to 60%.

13. The laminated gas sensor element according to claim 11, wherein the first protective layer, the second protective layer and the third protective layer each has a thickness in a range of 150 μm to 250 μm.

* * * * *